United States Patent [19]

Blackburn et al.

[11] Patent Number: 5,760,026
[45] Date of Patent: Jun. 2, 1998

[54] METHOD FOR TREATING MASTITIS AND OTHER STAPHYLOCOCCAL INFECTIONS

[75] Inventors: Peter Blackburn, New York; June Polak, Brooklyn, both of N.Y.

[73] Assignee: Ambi Inc., Tarrytown, N.Y.

[21] Appl. No.: 303,551

[22] Filed: Sep. 9, 1994

Related U.S. Application Data

[63] Continuation of Ser. No. 935,121, Aug. 20, 1992, abandoned, which is a continuation of Ser. No. 535,286, Jun. 8, 1990, abandoned, which is a continuation of Ser. No. 188,183, Apr. 28, 1988, abandoned, which is a continuation-in-part of Ser. No. 48,412, May 11, 1987, abandoned.

[51] Int. Cl.$^6$ ........................................... A61K 31/43
[52] U.S. Cl. ................................................. 514/192
[58] Field of Search ................................... 514/192

[56] References Cited

U.S. PATENT DOCUMENTS

| | | | |
|---|---|---|---|
| 3,278,378 | 10/1966 | Schindler et al. | 167/65 |
| 3,398,056 | 8/1968 | Zygmunt et al. | 195/80 |
| 3,427,377 | 2/1969 | Baver et al. | 424/7 |
| 3,594,284 | 7/1971 | Zygmunt et al. | 195/96 |
| 3,636,194 | 1/1972 | Parizeau | 424/115 |
| 4,011,312 | 3/1977 | Rueter et al. | 424/78 |
| 4,931,390 | 6/1990 | Rescei | 435/183 |

OTHER PUBLICATIONS

N. Craven et al., "pH–dependent Penicillin Tolerance May Protect Intraleukocytic *Staphylococcus aureus* from killing by Cloxacillin," 21 Antimicrobial Agents & Chemotherapy 618 (1982).
Khan et al., J. Dairy Sci 52, 895.
The Vet Clinics of North America, vol. 6, No. 2 (1984) Jarret, W.B. Saunders Co. pp. 338–343.
The Merck Manual, Fifth Edition, Merck & Co. (1979) p. 841.
E.F. Harrison et al., "Comparative In Vitro Activities of Antibiotics on Clinical Isolates of *Styphylococcus aureus*," 13 Applied Microbiol 212 (1965).
W.A. Zygmunt et al., "Susceptibility of Coagulase–negative Staphylococci to Lysostaphin and Other Antibiotics," 16 Applied Microbiol. 1168 (1968).
G. Pulverer et al., "Susceptibility of *Staphylococcus epidermidis* to Lysostaphin and Major Antimicrobial Agents," 19 Chemotherapy 109 (1973).
W. Schaffner et al., "Lysostaphin: An Enzymatic Approach to Staphylococcal Disease. I. In Vitro Studies," 39 Yale J. Biol. & Med. 215 (1967).
B.F. King et al., "Facile Penetration of the *Staphylococcus aureus* Capsule by Lysostaphin," 29 Infection & Immunity 892 (1980).
K.E. Quickel, Jr. et al., "Efficacy and Safety of Topical Lysostaphin Treatment of Persistent Nasal Carriage of *Staphylococcus aureus*," 22 Applied Microbiol. 446 (1971).
E.F. Harrison et al., "Antigenic Response to Topically Applied Proteins," 11 Infection & Immunity 309 (1975).

F.R. Stark et al., "Systemic Lysostaphin in Man—Apparent Anti–Microbial Activity in Neutropenic Patient," 291 Medical Intelligence 239 (1974).
Dixon et al., "Lysostaphin: An Enzymatic Approach to Staphylococcal Disease. III. Combined Lysostaphin–Methicillin Therapy of Established Staphylococcal Abscesses in Mice," 41 Yale J. Biol. & Med. 62, (1968).
R.R. Martin et al., "The selective activity of lysostaphin in vivo," 70 J. Laboratory & Clinical Medicine 1 (1967).
R.R. Martin et al., "The reacqui–sition of staphylococci by treated carriers: A demonstration of bacterial interference," 71 J. Laboratory & Clinical Med. 791 (1968).
W.A. Zygmunt et al., "Lysostaphin: Model for a Specific Enzymatic Approach to Infectious Disease," 16 Prog. Drug Research 309 (1972).
M.L. Garcia et al., "Characterization of Staphylococci Isolated From Mastitic Cows in Spain," 39 Applied Environ. Microbiol. 548 (1980).
L. Gutierrez et al., "Sensitivity of Lysostaphin as a Criterion for the Identification of Staphylococci from Animal Origin," 50 J. Applied Bacteriol 541 (1981).
B.A. Gunn et al., "Comparison of Methods for Identifying Staphylococcus and Micrococcus spp.," 14 J. Clinical Microbiol. 195 (1981).
P.J. Severance et al., "Rapid Identification of *Staphylococcus aureus* by Using Lysostaphin Sensitivity," 11 J. Clinical 724 (1980).
N. Craven et al., "pH–dependent Pencillin Tolerance May Protect Intraleukocytic *Staphylococcus aureus* from Killing by Cloxacillin," 21 Antimicrobial Agents & Chemotherapy 618 (1982).
P.J. van den Broek et al., "Adherence of Lysostaphin to and Penetration Into Human Monocytes," 21 Scand J. Immunol 189 (1985).
N. Craven et al., "The effects of cloxacillin on staphylococci phagocytosed by bovine neutrophils," 29 Research in Veterinary Science 57 (1980).
N. Craven et al., "Antibiotic activity against intraleukocytic *Staphylococcus aureus* in vitro and in experimental mastitis in mice," 44 Amer. J. Vet. Res. 709 (1983).
N. Craven et al., "Enhanced Killing of Penicillin–Treated *S. Aureus* by Host Defences: Effects of Amoxycillin, Cloxacillin and Nafcillin in vitro and in Experimental Mastitis," 5 Comp. Immum. Microbiol. Infect. Dis. 447 (1982).

(List continued on next page.)

*Primary Examiner*—Kevin E. Weddington
*Attorney, Agent, or Firm*—White & Case L.L.P.

[57] ABSTRACT

Lysostaphin is used to eliminate and cure staphylococcal infections including the cure of mastitis by intramammary infusion. Administration of from 2 mg to 400 mg of lysostaphin to an infected bovine mammary gland eliminates staphylococci, and the reoccurrence common with antibiotic therapy is not observed. Teat-dips containing lysostaphin, mutanolysin and lysozyme can be used as a prophylactic. Synergistic enhancement of the killing effect of lysostaphin is observed when a mild surfactant or penicillin or both is included in the formulation.

5 Claims, 1 Drawing Sheet

OTHER PUBLICATIONS

M.J. Paape et al., "Measurement of Phagocytosis of $^{32}$P–Labeled *Staphylococcus aureus* by Bovine Leukocytes: Lysostaphin Digestion and Inhibitory Effect of Cream," 36 Amer. J. Vet. Res. 1737 (1975).

R.K. Root et al., "Interactions Between Antibiotics and Human Neutrophils in the Killing of Staphylococci,"67 J. Clinical Invest. 247 (1981).

G. Ziv. et al., "Influence of antibiotics and intramammary antibiotic products on phagocytosis of *Staphylococcus aureus* by bovine leukocytes," 44 Amer. J. Vet. Res. 385 (2983).

N. Craven et al., "Phagocytosis of *Staphylococcus aureus* by Bovine Mammary Gland Macrophages and intracellular protection from antibiotic action in vitro and in vivo," 51 J. Dairy Research 513 (1984).

J.S. McDonald "Streptococcal and Staphylococcal Mastitis," 6 Vet. Clinics No. Amer. Large Animal Practice 269 (1984).

A. Franklin et al., "Antimicrobial Drug Susceptibility of *Staphylococcus aureus* Strains Isolated from Bovine Milk," 34 Nord. Vet.–Med. 460 (1983).

R.J. Yancey, Jr. et al., "Efficacy of lincosaminide antibiotics in the treatment of experimental staphylococcal mastitis in lactating mice," 15 J. Antimicrobial Chemotherapy 219 (1985).

N. Craven et al., "Penicillin (cloxacillin)–tolerant *Staphylococcus aureus* from bovine mastitis: identification and lack of correlation between tolerance in vitro and response to therapy in vivo," 34 Research Vet. Sci. 266 (1983).

G. Cisani et al., "High–Level Potentiation of Lysostaphin Anti–Staphylococcal Activity by Lysozyme," 21 Antimicrobial Agents and Chemotherapy 531 (1982).

Hirt et al., J. Reticuloendothelial Soc. 13, 27–46 (1973).

Rayburn et al., Clinical Research, p. 607A.

Mansour et al., Amer. Soc. Microbiol. Annual Meeting Abstract D69 (1983).

Frederick et al. Ann. Rev. Resp. Dis 133, A68 (1986).

G.L. Mandell, J. Clinical Investigation 52, 1673–1679 (1973).

J.N. Sheagren, New England J. Medicine 310, 1437–1442 (1984).

Severance et al., J. Clinical Microbiol. 12, 709–710 (1984).

Martin et al., Clinical Research, 341 (19 ).

Gunn et al., 214 (19 ).

M.G. Koenig, J. Infect. Dis 119, 101–102 (1969).

Schaffner et al., Clinical Research, 343 (19 ).

Jones et al., Henry Ford Hosp. Med. J. 16, 234–238 (1968).

Quinn et al., Antimicrobial Agents and Chemotherapy 1966, 382–388 (1967).

Khan et al., J. Dairy Sci 52, 895.

Kato et al., Bikin J. 29, 39–44 (1986).

D.E. Rogers, Posteopy Mikrobiologii 5, 279–296 (1966).

Plhackova et al., Folia Microbiol. 16, 517 (1971).

G. Pulverer, Dtsch med. Wschr 92, 2236–2238 (1967).

Dixon, R. E., Goodman, J.S., and Koenig, M.G., Lysostaphin: An Enzymatic Approach to Staphylococcal Disease. III. Combined Lysostaphin–Methicillin Therapy of Established Staphylococcal Abscesses In Mice. Yale J. Biol. Med, 41:62–68, 1968.

The Merck Veterinary Manual, Fifth Ed. Merck & Co (1979) p. 841.

Formulation of Veterinary Dosage Forms, J. Blodinger (ed), Marcel Dekker, Inc, (New York Msal Basel ) 1983, pp. 155–156.

The Merck Index, 10th ed, (Merck & Co, Inc, 1983) #5457, p. 5459.

*Am. J. Vet. Res.*, vol. 44, No. 4, pp. 709–712 Apr. 1983.

The Merck Veterinary Manual, Fifth Edition, Merck & Co. (1979) pp. 840 & 842–849.

The Vet. Clinics of North America, vol. 6/No. 2 Jul. 1984 Jarrett, W.B. Saunders Co. pp. 338–343.

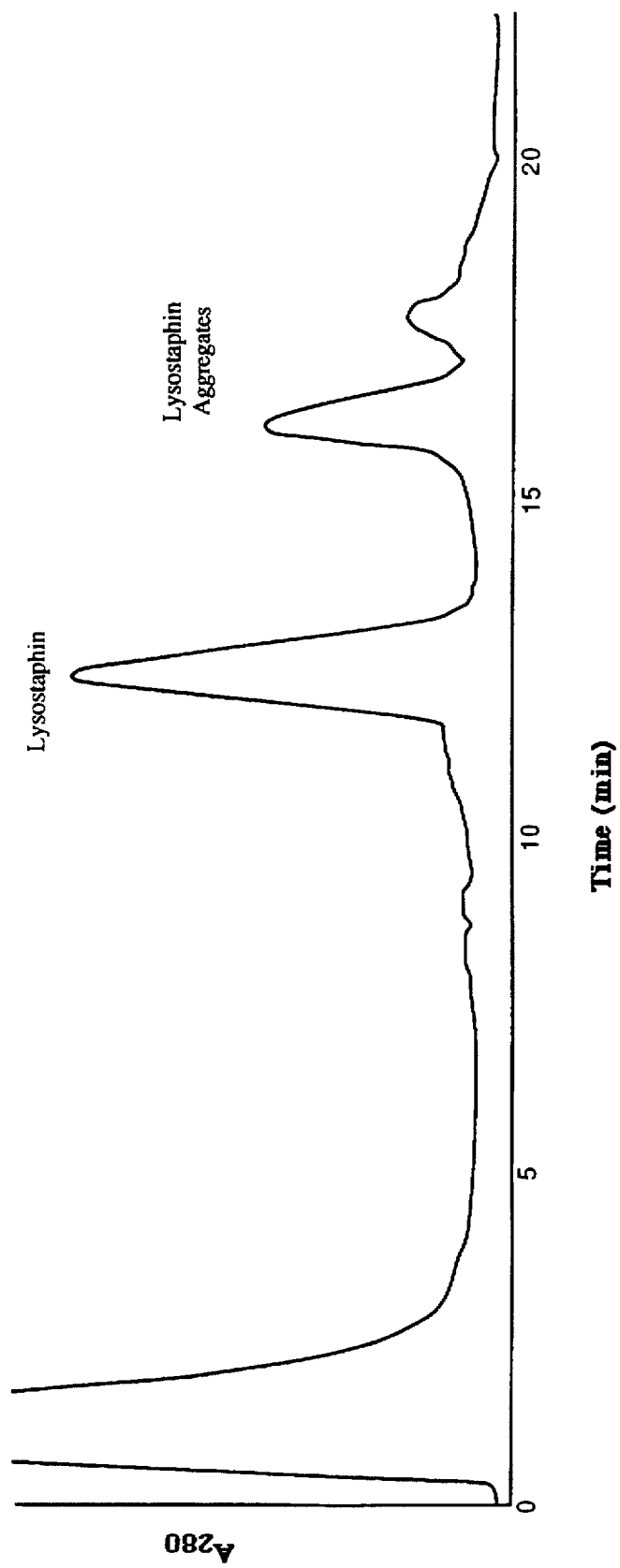
Fig 1: High Performance Liquid Chromatography of Lysostaphin

METHOD FOR TREATING MASTITIS AND OTHER STAPHYLOCOCCAL INFECTIONS

This application is a continuation of application Ser. No. 07/935,121, filed on Aug. 20, 1992, now abandoned, which is a continuation of application Ser. No. 07/535,286 (abandoned), filed Jun. 8, 1990, which is a continuation of application Ser. No. 07/188,183, filed Apr. 28, 1988 (abandoned), which is a continuation-in-part of application Ser. No. 07/048,412, filed May 11, 1987 (abandoned).

BACKGROUND OF THE INVENTION

This application relates to the use of lysostaphin in the treatment and prevention of staphylococcal infection and, in particular, to the treatment and prevention of staphylococcal bovine mastitis.

Lysostaphin is a bacteriocin secreted by a single known strain of *Staphylococcus simulans* originally isolated and named *Staphylococcus staphylolyticus* by Schindler and Schuhardt. The production of lysostaphin by *S. staphylolyticus* has been described previously in U.S. Pat. No. 3,278,378 issued Oct. 11, 1966 and in Proceedings of the National Academy or Sciences, Vol. 51, pp. 414–421 (1964). The single organism *S. staphylolyticus* (NRRL B-2628) which produced lysostaphin was recently identified as a biovar of *S. simulans* by Sloan et al., Int. J. System. Bacteriol., Vol. 32, pp. 170–174 (1982). Since the name *S. staphylolyticus*, is not on the Approved List of Bacterial Names, the organism producing lysostaphin has been redesignated as *S. simulans*.

Bacteriocins are proteins secreted by bacteria that kill and sometimes lyse related bacteria. For example, lysostaphin lyses and kills practically all known staphylococcal species but is inactive against bacteria of all other genera. Lysostaphin, isolated from culture filtrates of *S. simulans* (NRRL B-2628) grown according to published references, is an endopeptidase which cleaves the polyglycine cross-links of the peptidoglycan found in the cell walls of *staphylococci*. In addition, cultures that produce lysostaphin appear to be resistant to its activities while cultures grown under non-lysostaphin producing conditions are sensitive.

Previous studies have shown that lysostaphin can be produced by fermentation techniques wherein *S. simulans* is grown in liquid culture. Such fermentation techniques are described in U.S. Pat. No. 3,278,378 issued Oct. 11, 1966 and in Proceedings of the National Academy of Sciences, Vol. 51, pp. 414–421 (1964). Various improvements in the production of lysostaphin by fermentation techniques have also been made as documented in U.S. Pat. Nos. 3,398,056, issued Aug. 20, 1968, and 3,594,284, issued Jul. 20, 1971. The latter two references disclose improvements to culture medium and inoculation techniques whereby the production of lysostaphin by fermentation can be accelerated and improved. Lysostaphin is produced by *S. simulans* during exponential growth as an inactive precursor. The proenzyme is converted to active mature enzyme by protease produced by stationary phase cultures of *S. simulans*.

In addition, lysostaphin can be produced by recombinant microorganisms, including strains of *E. coli, Bacillus subtilis* and *B. sphaericus* which express the lysostaphin gene. In contrast to the natural production, lysostaphin accumulates during exponential growth in the culture medium of recombinant lysostaphin producing strains as fully processed mature active enzyme and is free of *staphylococcal* immunogenic contaminants.

Bovine mastitis is a costly problem to the dairy industry, costing over $2 billion per year in the United States alone. The disease is estimated to affect 50 per cent of American dairy cows to some degree, leading to unusable milk, decreased milk production, and, in cases of severe infection, the death of the animal.

Mastitis is caused by infection of the milk glands, principally by *Staphylococcus aureus* or *Streptococcus agalactiae*, and to a lesser degree by *E. coli* and other gram-negative bacteria or combinations thereof. Most streptococcal infections have proven to be effectively treatable using conventional antibiotic therapy. Staphylococcal mastitis has, however, proven more difficult to cure.

Traditional prevention of bovine mastitis can involve a complex regimen of daily teat-dipping with a disinfectant solution. (See, J. S. McDonald, 6 *Veterinary Clinics of North America Large Animal Practice* 269 (1984)) and may, in some cases, involve antibiotic-containing teat dips. Routine antibiotic therapy must be approached with caution, however, to minimize selection for antibiotic resistant strains. When infection does occur, intramammary infusion of antibiotics is indicated. Antibiotic therapy of this kind can reduce the infection so that the milk produced is saleable, but it generally does not lead to complete elimination of the causative organism.

In the past, staphylococcal mastitis has shown a poor response to antibiotic therapy and a tendency for infections to recur and become chronic. Studies on mastitis have indicated that part of the problem in treating mastitis is that a significant number of staphylococci remain viable in the mammary gland within phagocytic polymorphonuclear neutrophil leukocytes (PMN). It is believed that the staphylococci within the PMN are protected from the effects of the antibiotic, and, when lysis of the leukocyte occurs, the phagocytized staphylococci may provide a renewed source of mastitis-producing staphylococcal regrowth.

Studies on the possible mechanism of antibiotic evasion of phagocytized staphylococci in mastitis treatment show that lysostaphin had been rejected as a candidate for destroying phagocytized staphylococci. Craven et al., 29 *Research in Veterinary Science* 57 (1980); Craven et al., 21 *Antimicrobial Agents and Chemotherapy* 618 (1982); Craven et al., 5 *Comp. Immun. Microbial. Infect. Dis.* 447 (1982)) Craven et al., 51 *Journal of Dairy Research* 513 (1984). In these experiments lysostaphin was used in vitro as a pretreatment to destroy extracellular staphylococci prior to exposing the phagocytized staphylococci to cloxacillin, gentamicin or lysostaphin. Craven et al.'s results strongly suggest that lysostaphin would have no effect on mastitis since intracellular staphylococci were still viable after 20 hours of incubation in a lysostaphin containing solution. 51 *Journal of Dairy Research at* 515–516, and Table 2.

Lysostaphin has also been reported to penetrate human monocytes. Since monocytes are a different cell type than PMNs, this human model is not likely to be applicable to the treatment of bovine mastitis (van den Broek et al., 21 *Scand. J. Immunol* 189 (1985)) Lysostaphin has also been shown to be effective in the treatment of staphylococcal renal abscesses in mice, particularly when used in sequence with the administration of methicillin. Dixon et al., 41 *Yale J. Biol. Med.* 62 (1968).

In man lysostaphin has also been used as a therapeutic agent for treatment of chronic nasal staphylococcal infections (Quickel, Jr. et al., 22 *Applied Microbiology* 446 (1971)). In one case of a resistant staphylococcal infection, lysostaphin was given systemically (Stark et al., 291 *Medical Intelligence* 239 (1974)). In general, however, there has been great skepticism and reluctance in the medical and veterinary communities concerning the systemic administration of lysostaphin. Lysostaphin was considered to be too highly immunogenic to have general use for anything but topical applications.

SUMMARY OF THE INVENTION

It has now been found that lysostaphin can be used with surprising effectiveness to prevent and/or cure staphylococcal mastitis, even in its chronic form, without any adverse immunogenic effects. As a prophylactic, lysostaphin can be introduced as part of a daily teat-dipping regimen. Lysostaphin can be used alone but preferably, the teat-dip will include lysostaphin; other bacteriolytic agents such as mutanolysin, a bacteriocin produced by *Streptococcus globisporus* which is effective against streptococci; and lysozyme, a muralytic enzyme which hydrolyzes the polysaccharide backbone of the peptidoglycan in the cell walls of Gram positive and Gram negative bacteria. The formulation may also contain a chelating agent such as ethylenediamine tetraacetate (EDTA); and a mild surfactant which has been found to potentiate the killing of the bacteria. Suitable mild surfactants include, inter alia, esters of polyoxyethylene sorbitan and fatty acids (Tween series), octylphenoxy polyethoxy ethanol (Triton-X series), n-Octyl-β-D-glucopyranoside, n-Octyl-β-D-thioglucopyranoside, n-Decyl-β-D-glucopyranoside, n-Dodecyl-β-D-glucopyranoside, and biologically occurring surfactants, e.g., fatty acids, glycerides, monoglycerides, deoxycholate and esters of deoxycholate.

In addition to the prophylactic use of the broad-spectrum teat dip, various components of the teat dip can be infused into the infected udder to eliminate the bacteria and cure mastitis, e.g., lysostaphin alone or with a mild surfactant which surprisingly potentiates the staphylocidal effect of lysostaphin more than 1000 times. Furthermore, the combination of lysostaphin and penicillin also exhibits synergy such that a 1000 fold increase in the killing of staphylococci is observed in vitro. Therefore, a formulation for therapeutic infusion can also include penicillin, or a mild surfactant, with or without a chelating agent.

Infusions of a therapeutically effective amount of lysostaphin, with or without surfactant, EDTA, penicillin or other potentiating agents, are used to achieve elimination of the staphylococcal infection. Preferably such infusions contain between 2 to 400mg lysostaphin when no potentiating agents are present. In combinations containing potentiating agents, the required effective doses of lysostaphin can be lowered (as a result of its synergistically enhanced activity) by as much as 1000-fold.

Synergistic bactericidal activity of lysostaphin and penicillin was observed even upon administration to penicillinase-positive *S. aureus* and methicillin-resistant *S. aureus* ("MRSA"). MRSA are usually resistant to multiple antibiotics and are particularly problematic, especially in humans, as well as difficult to kill. The lysostaphin/penicillin combination would be indicated for use in specific situations where grave MRSA infection cannot be controlled by conventional antibiotic (e.g. penicillin) therapy. In addition, penicillin and other similar acting substances may also be useful together with lysostaphin as an agent against staphylococcal infection and contamination.

While the utility of the lysostaphin containing formulations according to the invention is illustrated using mastitis treatment, the enhanced effectiveness of the lysostaphin in these formulations makes them suitable for a number of other applications involving staphylococcal infection and contamination. Thus, the formulations could be used to control staphylococcal infections by incorporating them into wound dressings and medications, disinfectant scrubs, wipes or lotions, or in surgical implants. The formulations might also be used for cleaning of medical instruments, and of floors, walls, bedding and the like in circumstances where environmental disinfection is desired. Other potential uses include use as a nasal infusion to reduce intra-nasal carriage of staphylococci, and food related uses such as treatment of meat, eggs, cheese and fish or food packaging and handling equipment.

BRIEF DESCRIPTION OF THE DRAWING

FIG. 1 shows a chromatogram of lysostaphin produced by transformant *B. sphaericus* strain OO containing the recombinant plasmid pBC16-1L which codes for lysostaphin.

DETAILED DESCRIPTION OF THE INVENTION

Lysostaphin for use according to the claimed invention can be obtained from either natural or recombinant sources. Preferably, the lysostaphin is obtained from *Bacillus sphaericus* strain OO containing a recombinant plasmid which directs the synthesis of lysostaphin, as this provides for both high levels of lysostaphin production substantially free from staphylococcal immunogenic contaminants and facile lysostaphin purification since the lysostaphin accumulates directly in the growth medium. *Bacillus sphaericus* transformants containing the plasmid pBC16-1L have been found to be particularly suited for this purpose, although other strains are also useful as a source of lysostaphin. One method for obtaining lysostaphin from micro-organisms transformed by recombinant plasmids containing the gene which codes for lysostaphin is fully disclosed in U.S. patent application 034,464, filed Apr. 10, 1987, which is a continuation-in-part of U.S. application 852,407. Both applications are incorporated herein by reference.

Method of Treatment

Prophylactic treatments for bovine mastitis according to the invention involve the use of lysostaphin-containing teat dips. Lysostaphin-containing teat dips provide effective prevention of bovine mastitis when used before and after every milking. Preferably, the preventative regimen is used for all cows in the herd. The teat dips comprise about 1.0 µg/ml lysostaphin in an acceptable carrier. In addition, teat dips for use according to the invention may include about 1.0 µg/ml mutanolysin, about 10 µg/ml lysozyme, and a mild surfactant. Acceptable carriers are those which provide a buffered medium of approximately pH 8.0 and include aqueous buffers or hydrophilic ointment bases. For example non-ionic detergents, fatty acids or other mild surfactants, protein carriers, such as serum albumin or gelatin, powdered cellulose and carmel can be used as a carrier. The teat dip according to the invention may also advantageously include chelating agents, such as EDTA, colorants, and humectants, such as glycerol or sorbitol.

Mutanolysin is obtained from *Streptomyces globisporus*. Lysozyme is obtained from chicken egg whites.

Intramammary infusion of lysostaphin can be used to effectively treat infected animals who have developed either chronic or acute staphylococcal bovine mastitis despite prophylactic treatment. A single dose of from 2 to 400 mg lysostaphin per milk gland will eliminate the infection and cure staphylococcal mastitis in most instances. Additional doses of lysostaphin may be indicated where the infection is persistent. Doses significantly higher than 400 mg are not recommended as they can lead to unwanted and potentially adverse side effects including transient swelling, tenderness, and reduced milk production. These effects are limited to the treated gland, however, so that higher doses to a single gland may be appropriate in severe and life-threatening situations. In life-threatening cases, the route of administration could also include sites other than the infected gland so as to achieve systemic delivery, i.e., intravenous, subcutaneous, or intramuscular, and rectal or oral administration of suitably encapsulated formulations in which the lysostaphin is protected from inactivation in the gut.

It has also been found that infusion of a combination of lysostaphin and penicillin is surprisingly much more efficacious than lysostaphin alone because of an apparent synergistically enhanced bactericidal activity of this combination. In addition, it is believed that the therapeutic lysostaphin formulation may also include other agents which potentiate the bactericidal activity of lysostaphin, for example, synthetic penicillins and other antibiotics, chelating agents, mild surfactants, (e.g., deoxycholate) and other membrane active agents which may facilitate penetration of lysostaphin to the site of infection. In formulations that include e.g., penicillin, the dosage of lysostaphin can be decreased as a result of the potentiated bactericidal activity of lysostaphin. Since too high a dose of lysostaphin can induce unwanted and potentially adverse side-effects, this synergistic effect is significant not only for efficacy but also for avoidance of potential side effects.

EXAMPLES 1-4

In vitro experiments were conducted to determine the bactericidal activity of lysostaphin, mutanolysin, and lysozyme compositions toward S. aureus and other mastitis pathogens. The protocol was as follows:

Protocol for Viable Cell Assays

1. Bacterial cells (generally $10^9$ cells/ml) from an overnight plate (incubated at 37° C.) were resuspended in Tris buffer (20 mM Tris, pH 8).

2. 10 µl of bacterial cell suspension and 1 ml of control and teat dip test formulation (i.e. milk, buffer, or buffered detergent etc., containing the lysostaphin composition) were combined.

3. The cells were incubated for various times at 370° C.

4 a. The bacterial suspensions were centrifuged for 2 minutes in benchtop microcentrifuge to pellet cells.

5. The pellet was washed twice with 1.0 ml Phage buffer.

6. The cells were resuspended in 1.0 ml of Phage buffer, serially diluted in Phage buffer as appropriate, and 100 µl were plated on GL agar (*S. aureus, E. coli, Klebsiella pneumoniae.*) or Trypticase Soy agar (*S. agalactiae*).

7. The plates were incubated overnight at 370° C. and control and test plates were scored for colony forming units, (hereinafter CFU), to determine percent survival.

Composition of Phage buffer:

50 mM Tris, pH 7.8; 1 mM $MgSO_4$; 4 mM $CaCl_2$; 100 mM NaCl; Gelatin, 1.0 g/l. (Phage buffer helps stabilize any protoplasts and spheroplasts that did not lyse during treatment).

Composition of GL agar per liter:

Difco casamino acids, 3.0 g; Difco yeast extract, 3.0 g; NaCl, 5.9 g; Na lactate (60% w/v), 3.3 ml; 25% (v/v) glycerol, 4.0 ml; agar, 15 g; pH adjusted to 7.8.

Composition of Trypticase Soy agar per liter:

Bacto Tryptone, 15 g; Bacto Soytone, 5 g; NaCl, 5 g; agar, 15 g; pH adjusted to pH 7.3.

The results of in vitro experiments demonstrating the bactericidal efficacy of various lysostaphin therapeutic formulations are presented in Tables IA–IC. The results are presented as the percent survivals for *S. aureus* strains Newbould 305, strain RN451, the penicillin resistant strains RN1753 (Penicillinase producer) and Col strain (methicillin resistant).

Table IA presents results -for formulations containing 1 µg/ml, 0.1 µg/ml, 0.01 µg/ml and 0.00 µg/ml (CNTRL) lysostaphin. As can be seen from these results all levels of lysostaphin tested were effective to kill the organisms in a buffer vehicle (50 mM Tris, pH 8.0). In a milk vehicle, only 1 µg/ml and 0.1 µg/ml reduced bacterial survival.

Table IB shows the effect of adding a mild non-ionic surfactant, octylphenoxyl polyethoxy (10) ethanol, (Triton X-l00), to the lysostaphin formulation. For example, less than 0.001% of the cells survive exposure to 0.1 µg/ml lysostaphin and 0.1% Triton X-100, while 2.2% and 7.7%, respectively, survived exposure to each compound alone. Even more surprising, less than 0.001% survival was observed for 0.01 µg/ml lysostaphin and 0.1% Triton X-100.

Table IC demonstrates the synergistic effect of lysostaphin/penicillin combinations on three strains of staphylococci. Depending on the doses of each, the combinations of lysostaphin plus penicillin can be 100 to 1000 times more effective than either lysostaphin or penicillin alone with all three strains.

Table ID demonstrates the effect of the combination of lysostaphin and penicillin compared with their sequential effect on *S. aureus*. *S. aureus* were suspended at $10^7$ cells/ml in milk and incubated for the times indicated in the table with either lysostaphin and penicillin together or sequentially. After incubation, samples were centrifuged to obtain cell pellets which were washed twice, resuspended in 1.0 ml Phage buffer, diluted and 100 µl plated on GL agar. Colony forming units (CFU) were scored after incubation overnight at 37° C. to determine percent survival relative to appropriate controls. The lysostaphin/penicillin combination, exhibits a synergistically enhanced bactericidal activity against *S. aureus* which is at least 3 orders of magnitude greater than that seen when the two agents are added sequentially.

TABLE IA

The Effect of Lysostaphin On The Viability of *S. Aureus*

| Strain | Vehicle | Incubation Time | % Survival | | | |
|---|---|---|---|---|---|---|
| | | | 1.0L | 0.1L | 0.01L | CNTRL |
| S. aureus Newbould 305 | Milk | 15' | 2.8 | 75.0 | 100 | 100 |
| | | 2 h | 0.1 | 82.0 | 100 | 100 |
| RN451 | Milk | 15' | <0.1 | 22 | 100 | 100 |
| | | 2 h | <0.01 | 41 | 100 | 100 |
| | Buffer | 2 h | nd | 2.2 | 20 | 100 |

TABLE IB

The Effect Of Non-Ionic Detergent On The Bactericidal Activity of Lysostaphin Toward *S. aureus*

| Strain | Vehicle | Incubation Time | % Survival | | | | | |
|---|---|---|---|---|---|---|---|---|
| | | | 0.1L | 0.01L | 0.1%T | 0.1L + 0.1%T | 0.01L + 0.1%T | CNTRL |
| S. aureus RN451 | Buffer + 0.1% Triton | 2 h | 2.2 | 20 | 7.7 | <0.001 | <0.001 | 100 |

TABLE IC

The Effect Of Penicillin On The Bactericidal Activity of Lysostaphin Toward *S. aureus*

| Strain | Vehicle | Incubation Time | % Survival | | | | | |
|---|---|---|---|---|---|---|---|---|
| | | | 0.1L | 0.01L | 0.1P | 0.1L + 0.1P | 0.01L + 0.1P | CNTRL |
| S. aureus RN451 | Milk | 30' | 19 | 100 | 76 | 2.8 | 45 | 100 |
| | | 2 h | 26 | 100 | 17 | <0.01 | 0.4 | 100 |
| RN1753 penicillinase positive | Milk | 2 h | 1.9 | 66 | (10P) 46 | (10P) <0.01 | (10P) 14 | 100 |
| Col methicillin resistant | Milk | 2 h | 1.0 | 100 | (10P) 67 | (10P) <0.01 | (10P) 0.5 | |

TABLE ID

A Comparison of the Effect of the Combination of Lysostaphin and Penicillin Versus Their Sequential Effects on the Survival of *Staphylcoccus aureus* (Strain RN451) in milk at 37° C.

| | combo(2 h) | lspn(2 h) | pen(2 h) | Pen(2 h)/ lspn(0.5 h) | lspn(2 h)/ pen(0.5 h) |
|---|---|---|---|---|---|
| % survival | 0.0005 | 23 | 25 | 0.3 | 10 | lspn = lysostaphin; pen = penicillin

In addition, assays for lysostaphin, mutanolysin, and lysozyme activities which measure the decrease in turbidity at 600 nm of suspensions of live *S. aureus*, *S. agalactiae*, and *E. coli* or *Klebsiella pneumoniae*, respectively, indicated that chelating agents (e.g., EDTA) potentiate the lytic activity of each of the three bacteriolytic enzymes.

The data indicate that lysostaphin is a rapidly acting, highly effective staphylocide, the bactericidal activity of which is potentiated more than 1000 times by penicillin or the mild surfactant, Triton X-100. The inclusion of a chelating agent further potentiates the bactericidal activity of lysostaphin. It is also believed that synthetic penicillins and cell wall-active antibiotics will potentiate the activity of lysostaphin. Lysostaphin is an effective staphylocide in milk, but in buffer the bactericidal activity of lysostaphin is approximately 10 times that observed in milk.

EXAMPLE 5

According to the general protocol described in Examples 1–4, further in vitro experiments were performed to evaluate the bactericidal activity of a lysostaphin composition comprising bacteriolytic enzymes, a non-ionic detergent and buffered chelating agent. As shown in Table II a formulation containing 1% Triton X-100, 0.1 µg/ml lysostaphin, 10 µg/ml lysozyme, and 5 mM EDTA in 20 mM Tris, pH 8.0, (AMBI Teat Dip-0.1) was extremely effective against a wide range of mastitis-causing pathogens, including *S. aureus* strain Newbould 305, *S. epidermidis*, *Streptococcus agalactiae* strain McDonald and strain C48, and clinical isolates of *Streptococcus uberis*, *E. coli*, and *Kiebsiella pneumoniae*.

TABLE II

In Vitro Efficacy Of AMBI Teat Dip-1 Against Mastitis Pathogens

| Strain | Viable Count | % Survival |
|---|---|---|
| Staphylococcus aureus (Newbould 305) | 7.0 × 10⁵ | <0.001 |
| Staphylococcus aureus (RN451) | 5.7 × 10⁵ | <0.001 |
| Staphylococcus epidermidis (PS) | 8.3 × 10⁵ | <0.001 |
| Streptococcus agalactiae (McDonald) | 3.9 × 10⁵ | <0.001 |
| Streptococcus agalactiae (C48) | 2.9 × 10⁴ | <0.001 |
| Streptococcus uberis (PS) | 6.9 × 10⁵ | <0.001 |
| Escherichia coli (PS) | 9.1 × 10⁵ | <1.0 |
| Klebsiella pneumoniae (PS) | 9.6 × 10⁵ | <1.0 |

EXAMPLE 6

Trials on cows were performed which demonstrated the efficacy of lysostaphin teat-dip compositions in vivo. The tests were performed generally according to Protocol A of the National Mastitis Council. In general, teats were cleaned with a 1% iodine wash solution and dried with a paper towel. Teats were then rinsed with alcohol and allowed to air dry. All four teats per cow were next dipped in a $10^8$ cell/ml suspension of S. aureus strain Newbould 305 to cover ½ the teat, and allowed to air dry for 30 minutes. Two teats (right fore and left rear) were then dipped in a lysostaphin test teat dip formulation (10 µg/ml lysostaphin in 0.85% saline) to cover ⅔ of the teat, and allowed to air dry for 30 minutes; the remaining two teats acted as non-treated controls. Each teat was first swabbed with a moist cotton swab and then washed with 10 ml of 0.85% sterile saline solution; the wash was collected into a sterile 30 ml tube. A 0.2 ml sample of the wash, and appropriate dilutions thereof, were plated on blood agar in duplicate and incubated at 370° C. for 24–48 hours. Colony forming units were determined and percent survival of S. aureus calculated relative to controls.

Ten µg/ml solutions of lysostaphin in 0.85% saline completely disinfected invading S. aureus from cow teat surfaces. Moreover, lysostaphin applied to teat surfaces prior to exposure of teats to S. aureus suspensions had sufficient residual activity on the teat surface to prevent colonization of the teat. Residual activity could be enhanced by inclusion of a polymeric adsorbent and/or inert carrier protein to reduce lysostaphin wash-off.

EXAMPLE 7

In accordance with the results from Example 6 and the data obtained in vitro, an enhanced teat dip formulation (AMBI Teat Dip 1.0) comprising 1.0 µg/ml lysostaphin, 10 µg/ml lysozyme, 1.0 % Triton X-100, and 5 mM EDTA in 20 mM Tris buffer, pH 8.0 was evaluated as a disinfectant against S. aureus strain Newbould 305. Teats were dipped in $10^8$ cells/ml S. aureus strain Newbould 305, and allowed to air dry for 30 min. The treated teats were then dipped in AMBI test teat dip-1.0 solution (1.0 ug/ml lysostaphin, 10.0 µg/ml lysozyme, 1.0% Triton X-100, 5 mM EDTA, 20 mM Tris buffer, pH 8.0) and allowed to air dry for 30 min. Teats were swabbed with a moist cotton swab, and rinsed with 10 ml sterile 0.85% saline. The swab and rinse were plated separately on blood agar plates, incubated 24–48h and CFU determined. The results, shown in Table IIIA clearly demonstrate the efficacy of this preparation. At least a 3 fold order of magnitude reduction was observed in the numbers of S. aureus recovered from treated teats; 50% of treated teats were free from invading S. aureus.

Corresponding tests were performed in which teats were dipped in preparations containing $2\times10^7$ cells/ml Streptococcus agalactiae strain McDonald, and then allowed to air dry for thirty minutes. The results of these tests are shown in Table IIIB. All of the treated teats were free of S. agalactiae.

TABLE IIIA

In Vivo Efficacy of AMBI Teat Dip-1.0 Against Staphylococcus aureus On Cow Teats

| Cow No. | CONTROL CFU's per ml | | CONTROL CFU's per ml | |
|---|---|---|---|---|
| | LF | RH | LH | RF |
| 1 | 225 | 1,675 | 13 | 0 |
| 2 | 24,500 | 19,500 | 8 | 175 |
| 3 | 300 | 15,000 | 0 | 15 |
| 4 | 78 | 155 | 0 | 150 |
| 5 | 50,500 | 18,750 | 5 | 8 |
| 6 | 44,250 | 65,500 | 0 | 0 |
| 7 | 75 | 43 | 35 | 3 |
| 8 | 175 | 1,150 | 0 | 0 |
| 9 | 68 | 58 | 0 | 5 |

TABLE IIIA-continued

In Vivo Efficacy of AMBI Teat Dip-1.0 Against Staphylococcus aureus On Cow Teats

| Cow No. | CONTROL CFU's per ml | | CONTROL CFU's per ml | |
|---|---|---|---|---|
| | LF | RH | LH | RF |
| 10 | 550 | 300 | 0 | 0 |
| Average | 12,072 | 12,213 | 6 | 36 |
| Total Qtrs Negative | 0/10 | 0/10 | 6/10 | 4/10 |

TABLE IIIB

In Vivo Efficacy of Teat Dip-1.0 against Streptococcus agalactiae (McDonald strain) on Cow Teats

| Cow. No. | CONTROL CFU's per ml | | TREATED CFU's per ml | |
|---|---|---|---|---|
| | LF | RH | LH | RF |
| 1. | 5 | 15 | 0 | 0 |
| 2. | 53 | 360 | 0 | 0 |
| 3. | 115 | 48 | 0 | 0 |
| 4. | 150 | 10 | 0 | 0 |
| 5. | 13,750 | 1,200 | 0 | 0 |
| 6. | 16,250 | 725 | 0 | 0 |
| 7. | 95 | 320 | 0 | 0 |
| 8. | 0 | 450 | 0 | 0 |
| 9. | 1,175 | 775 | 0 | 0 |
| 10. | 150 | 300 | 0 | 0 |
| Average | 2,574 | 420 | 0 | 0 |
| Total Qtrs negative: | 1/10 | 0/10 | 10/10 | 10/10 |

EXAMPLE 8

Guinea pig mammary glands were infected with 200–300 CFU of S. aureus strain Newbould 305. Three days post-infection, the glands were infused with a single dose of lysostaphin dissolved in 200 µl 0.85% sterile saline. Milk samples were collected from the glands 6 hours after treatment and at 12 hour intervals thereafter for at least 5 days after treatment. 100 µl milk samples from treated and nontreated infected glands were plated on blood agar. After 24–48 hours incubation, the plates were counted to determine CFU. The single doses of lysostaphin which were sufficient to eliminate the infection did not produce adverse side effects and indicated that intramammary infusions of lysostaphin are effective against staphylococcal mastitis. At 125 µg/kg, glands were cleared of infection by the 6 hour post-treatment sample and remained clear throughout the study.

TABLE IV

Efficacy of Intramammary Infusion of Lysostaphin Toward Experimental STAPHYLOCOCCAL Mastitis in Guinea Pig

| | Lysostaphin Dose µg/kg | | | | | |
|---|---|---|---|---|---|---|
| | ZERO | 1.0 | 5.0 | 25.0 | 62.5 | 125.0 |
| Number of animals cleared of infection | (0/10) | (1/0) | (1/2) | (2/2) | (1/1) | (7/7) |

It can be seen from these examples that lysostaphin is effective for treatment of staphylococcal mastitis and that its effect is greatly enhanced when used in combination with penicillin or with substances such as mild surfactants and chelating agents.

Production of Lysostaphin from Bacillus

Lysostaphin for use according to the claimed invention can be obtained from either natural or recombinant sources. Preferably, the lysostaphin is obtained from cultures derived from *Bacillus sphaericus* strain 00 transformed by recombinant plasmids which direct lysostaphin synthesis as described in copending application Ser. No. 034,464 filed Apr. 10, 1987 which is a continuation-in-part of Ser. No. 852,407 filed Apr. 16, 1986. This method provides for both high levels of lysostaphin production substantially free from staphyloccal immunogenic contaminants. Lysostaphin purification is facilitated since active lysostaphin accumulates directly in the growth mediums Using this method, *Bacillus sphaericus* 00 transformants containing plasmid PBC16-1L (*B. sphaericus* 00/pBC16-1L) have been found to be particularly suited for the purpose, although other transformed Bacillus strains are also useful as a source of lysostaphin.

The lysostaphin-producing organism is grown under conditions conducive to the production of lysostaphin. The optimum conditions will vary from strain to strain; however, certain types of growth media and fermentation conditions are known to enhance lysostaphin production. In the case of the *Bacillus sphaericus* 00/pBC16-1L transformant, the preferred growth medium is VY broth (25 g Veal Infusion+5 g Yeast Extract/liter) under well-aerated conditions (see Table V).

TABLE V

Effect of Aeration on Lysostaphin Production
by the Bacillus Sphaericus 00/pBC 16-1L Transformant

| | Stirring Speed | | | |
|---|---|---|---|---|
| Klett | 100 rpm | 200 rpm | 200 rpm (Fluted) | 320 rpm |
| 250 | 21.8 | 36.2 | 35.9 | 30.0 |
| 350 | 40.1 | 68.9 | 45.3 | 45.0 |
| 400 | 88.5 | 62.7 | 102.8 | 71.4 |
| 450 | n/a | 86.4 | 52.3 | 135.9 |
| O/N | 64.4 | 31.3 | 37.6 | 57.5 |

Cultures (40 ml) in 300 ml Klett flasks were inoculated with 4 ml of overnight primary culture. Growth medium: VY broth containing 5 μg/ml erythromycin.

Samples were removed at times throughout growth. Supernatants were assayed for lysostaphin activity by turbidometric clearing of dead cell suspensions of *S. aureus*. Results are presented as μg lysostaphin per ml. *B. sphaericus* 00/pBC16-1L transformant grown on VY medium produced and secreted approximately 130 mg lysostaphin per liter of culture medium, which is more than four times the amount produced by *S. simulans* under the best fermentation conditions currently available. Lysostaphin accumulates in the growth medium with little or no degradation, even after prolonged incubation of cultures, and accounts for more than 80% of total extracellular protein.

Lysostaphin is isolated from the growth medium in accordance with known fractional precipitation (salting out) procedures. Alternatively, a particularly effective purification is achieved by combining a precipitation and a chromatographic separation of the fermentation broth from cultures of the lysostaphin-producing *B. sphaericus* 00/pBC16-1L transformant.

Cells are removed from the fermentation broth, for example by centrifugation or ultrafiltration, and solid ammonium sulfate is added to the supernatant to 40–60%, preferably 50%, of saturation. After 1 hour at 4° C., the lysostaphin-containing precipitate is recovered by centrifugation. Recovery at this step is greater than 80%.

The precipitate is redissolved in a minimum volume of 10 mM sodium phosphate buffer (pH 7.00, 50 mM NaCl) and dialyzed against 100 volumes of the same buffer. After removal of any particulate material, the dialyzed solution is chromatographed on a cation exchange column (preferably Pharmacia FPLC Mono S) and eluted using a buffered gradient of increasing salt concentration from 0.05 to 0.25M NaCl. Recovery of lysostaphin for the single chromatographic step was more than 90%. Lysostaphin activity is associated with two major peaks (FIG. 1). The later eluting peak of lysostaphin is comprised of non-covalent aggregates of the protein. These aggregates dissociate on dilution in buffer and under conditions of sodium dodecylsulfate polyacrylamide gel electrophoresis.

Construction of the plasmid vector pBC16-1L which contains the gene coding for lysostaphin Lysostaphin-producing strains of *Bacillus sphaericus* can be produced using recombinant DNA techniques and preferably those described in copending applications 852,407 and 034,464. Specifically, total *S. simulans* DNA is partially cleaved by the appropriate restriction endonuclease and DNA fragments so generated are then ligated to a linearized known vector (pUC8) with compatible ends, carrying an antibiotic resistance marker and the lac Z' gene (i.e. β-galactosidase gene). The ligation mix is then transferred to *E. coli* (JM105) by transformation. Successful insertions of the lysostaphin gene into the plasmid can be found by selecting for transformants by growth on the appropriate antibiotic, and then finding those with a lac Z' negative phenotype. Lysostaphin production is detected by turbidometric clearing of a suspension of *S. aureus* either in solution format or as an overlay on agar plates.

Using various lysostaphin-producing *E. coli* JM105 transformants, restriction analysis and subcloning of the JM105 plasmid DNA showed that the DNA sequence coding for lysostaphin was localized to a 1.5 kbp Hpa II-Hind III DNA fragment. This fragment was visualized after electrophoresis by ethidium bromide staining and transferred to a nitrocellulose filter strip. The strip was washed with NET buffer (0.15M NaCl, 0.1 m EDTA, 0.02M Tris, pH 8.0) and the transferred DNA was eluted by incubation of the strip in NET buffer containing 1M NaCl for 1 hour at 65° C., Ethidium bromide was removed from the DNA by extraction with n-butanol. DNA, precipitated by addition of two volumes of cold 95% ethanol to the aqueous phase, was collected by centrifugation, washed with 80% ethanol and dissolved in TE buffer (10 mM Tris, 1 mM EDTA, pH 8.0). Recombinant plasmids capable of transforming *B. subtilis* as well as *B. sphaericus* to express lysostaphin were constructed using a derivative of plasmid pBC16 (pBC16-1) as a cloning vector. pBC16 is a tetracycline resistant (Tet $^r$) Bacillus plasmid, originally isolated from *B. cereus* (K. Bernhard, H. Schremph, and W. Goebel, 133 *J. Bact.* 897, 1978). Plasmids indistinguishable from pBC16 by restriction analysis and Southern Hybridization were also found in soil isolates of *B. subtilis* and *B. sphaericus* (J. Polak and R. N. Novick, 7 *Plasmid* 152, 1982).

The pBC16 derivative (pBC16-1) used as the cloning vector was constructed by ligating the TaqIA fragment of plasmid pE194 (B. Weisblum, M. Y. Graham, T. Gryczan, and D. Dubnau, 137 *J. Bact.* 635, 1979), an erythromycin resistant (erm$^r$) plasmid from *S. aureus*, with a partial TacI digest of plasmid pBC16 using T4 Ligase. After transfer of the ligation mixture to *B. subtilis* by protoplast transformation (S. Chang and S. N. Cohen, 168 *Molec. Gen. Genet.* 111, 1979), clones that were resistant to both tetracycline and erythromycin were selected. One such clone was designated pBC16-1.

Restriction analysis revealed that pBC16-1 contained all of the pBC16 TaqI fragments plus the TaqIA fragment of pE194 which contains the erythromycin resistance determinant. pBC16-1 was then digested with the restriction endonuclease PvuII, thereby removing about 25% of the plasmid DNA including most of the tetracycline resistance determinant. The Pvu II-digested vector pBC16-1 was treated with calf intestinal alkaline phosphatase. The 1.5 Kbp DNA fragment which codes for lysostaphin was treated with the Klenow fragment of DNA polymerase. The 1.5 Kbp DNA fragment and plasmid DNA were then mixed and ligated using T4 ligase, and the ligation mixture was transferred to *B. subtilis* by protoplast transformation. Transformants were resistant to erythromycin, sensitive to tetracycline, and produced lysostaphin as indicated by zones of clearing when grown on agar containing dead *S. aureus* cells. One such lysostaphin producing clone was picked and designated *B. subtilis*/pBC16-1L. Plasmid pBC16-1L DNA extracted from the *B. subtilis*/pBC16-1L transformant was isolated after ultracentrifugation in an ethidium-bromide cesium chloride density gradient. Plasmid pBC16-1L DNA was transferred by protoplast transformation to various species of Bacillus, including *B. sphaericus* strain OO. Transformants were resistant to erythromycin and produced lysostaphin. The *B. sphaericus* OO/pBC16-1L transformant provides maximum production of lysostaphin and permit accumulation of intact, enzymically active product. *B. sphaericus* strain OO was originally isolated from soil and is maintained in the culture collection (PRN3106) of the Public Health Research Institute, New York, N.Y. *B. sphaericus* OO/pBC16-1L is maintained in the culture collection of the Public Health Research Institute, New York, N.Y. and has been deposited with the American Type Culture Collection under ATCC Accession No. 67398.

We claim:

1. A method of treating recurring staphylococcal mastitis resulting from intracellular *Staphylococcus aureus* comprising administering to an infected gland by intramammary infusion a therapeutic agent consisting essentially of the bacteriocin lysostaphin produced by recombinant means in a pharmaceutically acceptable carrier in an amount effective to eliminate the recurring staphylococcal mastitis.

2. A method according to claim 1, wherein from 2 mg to 400 mg of lysostaphin is administered to a bovine mammary gland.

3. A method according to claim 1, wherein the therapeutic agent further comprises a mild surfactant in an amount effective to potentiate the therapeutic effect of the lysostaphin.

4. A method according to claim 1, wherein the therapeutic agent further comprises at least one agent which potentiates the bactericidal activity of lysostaphin selected from the group consisting of penicillin, synthetic penicillins, bacitracin, methicillin, cephalosporin, polymyxin and chelating agents in an amount effective to synergistically enhance the therapeutic effect of the lysostaphin.

5. A method according to claim 4, wherein the therapeutic agent further comprises a mild surfactant in an amount effective to potentiate the therapeutic effect of the lysostaphin.

* * * * *